United States Patent
Bassine (10) Patent No.: US 10,215,166 B2
(45) Date of Patent: Feb. 26, 2019

(54) MEDICAL AIR COMPRESSOR

(71) Applicant: Stuart H. Bassine, Butler, TN (US)

(72) Inventor: Stuart H. Bassine, Butler, TN (US)

(*) Notice: Subject to any disclaimer, the term of this patent is extended or adjusted under 35 U.S.C. 154(b) by 163 days.

(21) Appl. No.: 15/394,123

(22) Filed: Dec. 29, 2016

(65) Prior Publication Data

US 2018/0187664 A1   Jul. 5, 2018

(51) Int. Cl.
| | |
|---|---|
| *F01B 1/02* | (2006.01) |
| *F04B 27/02* | (2006.01) |
| *F04B 27/073* | (2006.01) |
| *F04B 39/00* | (2006.01) |
| *F16H 21/20* | (2006.01) |
| *A61M 16/10* | (2006.01) |
| *F04B 9/04* | (2006.01) |
| *F04B 27/00* | (2006.01) |
| *F04B 27/06* | (2006.01) |
| *F04B 35/01* | (2006.01) |
| *F04B 53/14* | (2006.01) |

(52) U.S. Cl.
CPC ............ *F04B 27/02* (2013.01); *A61M 16/10* (2013.01); *F04B 9/045* (2013.01); *F04B 27/005* (2013.01); *F04B 27/0657* (2013.01); *F04B 27/073* (2013.01); *F04B 35/01* (2013.01); *F04B 39/0022* (2013.01); *F04B 53/144* (2013.01); *F16H 21/20* (2013.01); *F04B 2201/1213* (2013.01)

(58) Field of Classification Search
CPC ................... F04B 9/045; F04B 2201/1213
USPC ............................................. 92/72
See application file for complete search history.

(56) References Cited

U.S. PATENT DOCUMENTS

| | | |
|---|---|---|
| 1,503,540 A | 8/1924 | Lawhead |
| 1,748,443 A | 2/1930 | Dawson |
| 3,002,504 A | 10/1961 | Taylor |
| 3,216,355 A | 11/1965 | Wanner |
| 3,300,997 A | 1/1967 | Kocher |
| 4,443,163 A | 4/1984 | Gaither |
| 5,076,769 A | 12/1991 | Shao |
| 6,162,030 A | 12/2000 | Pierrat |

(Continued)

FOREIGN PATENT DOCUMENTS

| | | |
|---|---|---|
| DE | 3211261 | 12/1983 |
| GB | 2421981 | 7/2006 |

(Continued)

OTHER PUBLICATIONS

European Patent Office (Saverio Ricci—Authorized officer), International search report and Written Opinion (17 pages); dated Mar. 9, 2018, dated Mar. 20, 2018.

*Primary Examiner* — Michael Leslie
(74) *Attorney, Agent, or Firm* — Luedeka Neely Group, P.C.

(57) ABSTRACT

A pump or compressor includes a rotating shaft, and at least a first piston rod substantially perpendicular to the rotating shaft and connecting a first pair of pistons at opposite ends of the piston rod. The piston rod moves back and forth relative to the rotating shaft. The compressor additionally includes a circular eccentric, and a circular ring connected to the circular eccentric via a bearing. A drive pin engages the circular ring at a fixed position on the circular ring and engages the at least a first piston rod. When rotational motion of the shaft rotates either the first piston rod and first pair of pistons or the circular eccentric, the drive pin and the first piston rod move back and forth relative to the rotating shaft.

19 Claims, 9 Drawing Sheets

(56) References Cited

U.S. PATENT DOCUMENTS

| | | | |
|---|---|---|---|
| 6,283,723 B1 | 9/2001 | Milburn et al. | |
| 2007/0258831 A1 | 11/2007 | Irick | |
| 2014/0369873 A1 | 12/2014 | Bassine | |

FOREIGN PATENT DOCUMENTS

| | | |
|---|---|---|
| JP | 2000-064953 | 3/2000 |
| WO | 8502232 | 5/1985 |
| WO | 2013106810 | 7/2013 |

MEDICAL AIR COMPRESSOR

BACKGROUND OF THE INVENTION

The invention relates particularly to the field of compact air compressors for medical use, such as for portable oxygen concentrators.

Embodiments of the invention are alternatives to the pump or compressor disclosed in International Application No. PCT/US2013/021394, published 18 Jul. 2013 as No. WO 2013/106810 A1, and U.S. patent application Ser. No. 14/370,707, published Dec. 19, 2014 as No. US 2014/0369873 A1, the entire disclosure of which is hereby incorporated by reference. In that pump or compressor, rotary motion of a shaft is converted to reciprocating motion of a piston rod by a mechanism which includes an eccentric groove in an end plate.

Pumps or compressors for fluid (including air, and gas in general) movement are known for the medical, automotive and beverage industries, as examples. Embodiments of the subject invention are particularly intended for and are useful as compact air compressors for medical use, such as for portable oxygen concentrators.

Piston pumps are well known, and traditionally include a rotating shaft having a concentric attached via a connecting rod to a reciprocating piston, such as are disclosed as "prior art" in publication Nos. WO 2013/106810 A1 and US 2014/0369873 A1.

SUMMARY OF THE INVENTION

In one aspect, a compressor is provided. The compressor includes a rotating shaft, and at least a first piston rod substantially perpendicular to the rotating shaft and connecting a first pair of pistons at opposite ends of the piston rod. The piston rod moves back and forth relative to the rotating shaft. The compressor additionally includes a circular eccentric, and a circular ring connected to the circular eccentric via a bearing. A drive pin engages the circular ring at a fixed position on the circular ring and engages the at least a first piston rod. When rotational motion of the shaft rotates either the first piston rod and first pair of pistons or the circular eccentric, the drive pin and the first piston rod move back and forth relative to the rotating shaft.

In another aspect, a compressor is provided. The compressor includes a rotating shaft, a first piston rod extending through the compressor in one direction substantially perpendicular to the rotating shaft and connecting a first pair of pistons at opposite ends of the first piston rod, and a second piston rod extending through the compressor in another direction substantially perpendicular to the rotating shaft and connecting a second pair of pistons at opposite ends of the second piston rod. The piston rods move back and forth relative to the rotating shaft. The compressor additionally includes a circular eccentric, and a circular ring connected to the circular eccentric via a bearing. A first drive pin engages the circular ring at a first fixed position and engaging the first piston rod and a second drive pin engages the circular ring at a second fixed position and engages the second piston rod. When rotational motion of the shaft rotates either the piston rods and pistons or the circular eccentric, the drive pins and the piston rods move back and forth relative to the rotating shaft.

DETAILED DESCRIPTION

In overview, embodiments of the subject invention provide compressors for various industrial environments, particularly compact air compressors for medical use. Embodiments of the invention benefit from high efficiency by allowing multiple pistons to be driven by a common shaft. Embodiments of the invention can minimize duplication of parts, and can provide assemblies which are lighter in weight compared to prior art compressors.

Pumps in general and compressors in particular embodying the invention accordingly are useful for moving or compressing fluids. The term "fluids" is used herein in its broadest sense to encompass any matter that flows and is subject to pressure, whether in gaseous or liquid form, including air and specific gases. In that regard, the compressor may be referred to as a fluid compressor, an oxygen compressor, or an air compressor. The nature of the medium being compressed does not change the structure.

Figure 1:
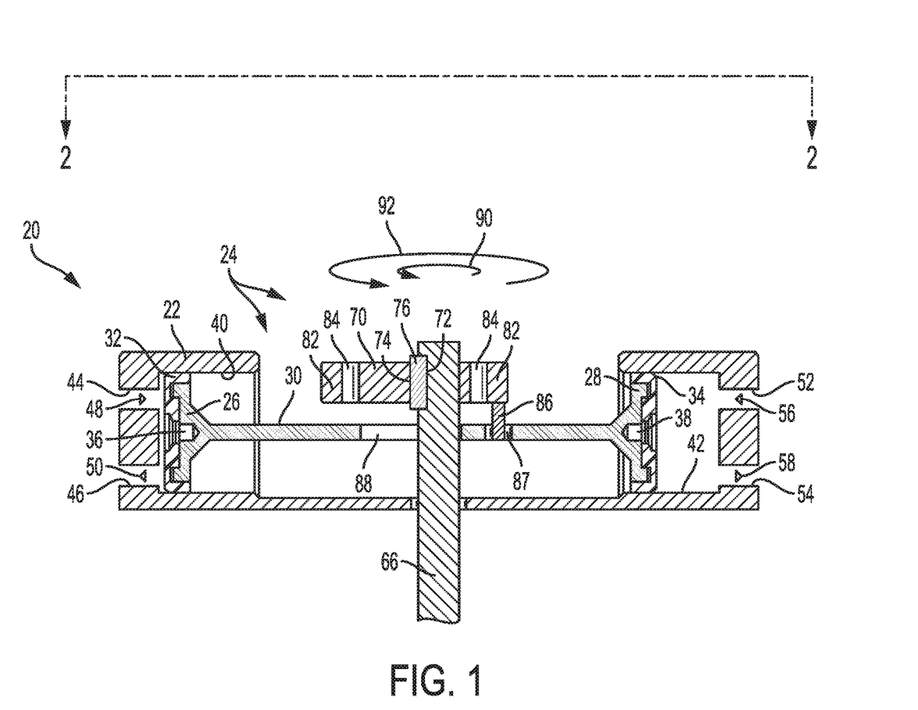
FIG. 1 is a sectional front sectional view of a first pump or compressor embodying the invention.
Figure 2:
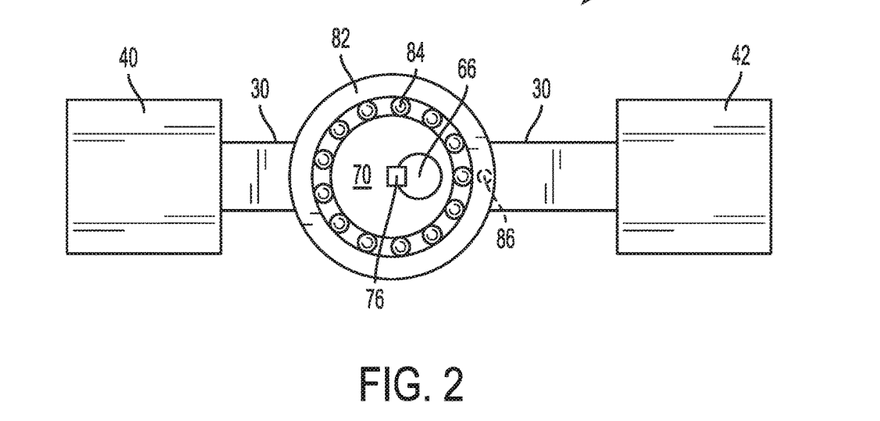
FIG. 2 is a partial top view, on line 2-2 of FIG. 1.
Figure 3:
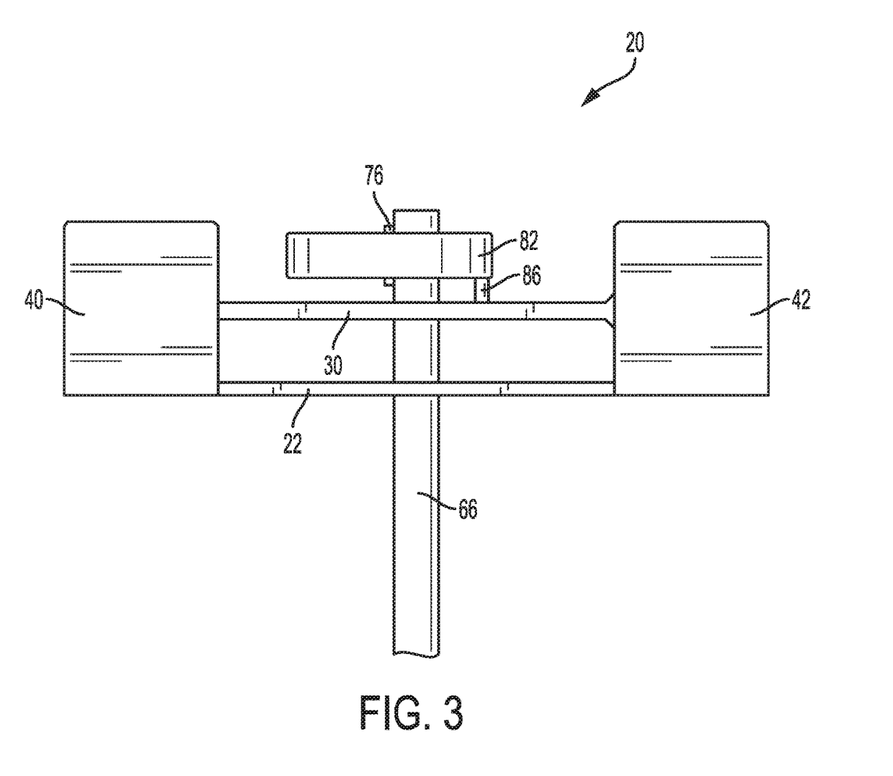
FIG. 3 is a front elevational view of the compressor of FIG. 1 in the same orientation as FIG. 1.

Referring first to FIGS. 1-3, illustrated as a representation and somewhat schematically is a first pump or compressor 20 embodying the invention. The pump or compressor 20 has a body generally designated 22, and includes a single pair 24 of pistons 26 and 28, which preferably are rectangular but which may be circular in cross section. The pistons 26 and 28 are attached at opposite ends of a piston rod 30. The pistons 26 and 28 have respective representative piston heads 32 and 34, which may also be referred to as seals 32 and 34. The piston heads 32 and 34 provide sealing and centering and, in the illustrated embodiment are made of a polytetrafluoroethylene (PTFE) plastic material such as Teflon® or Rulon®. By way of example, the piston heads 32 and 34 are secured by machine screws 36 and 38. It will be appreciated that the illustrated construction is representative only, and that various forms of seals and seal mountings may be employed. For example, flat round washers (not shown) and screws may be employed. What is important is that the seals extend radially beyond the pistons 26 and 28.

The piston rod 30 is unitary. In other words, the piston rod 30 is a single, continuous piece along its length between the pistons 26 and 28. In addition, the piston rod 30 has no bearings or other support, other than by the pistons 26 and 28 (more particularly by the piston heads or seals 32 and 34).

The pistons 26 and 28 reciprocate within respective individual piston chambers 40 and 42, which may in accordance with conventional terminology be termed cylinders 40 and 42, although the piston chambers 40 and 42 are not necessarily circular in cross section and accordingly not necessarily cylindrical. (Thus, although the term "cylinder" is employed herein, the piston chambers 40 and 42 may very well be rectangular in cross section.) The piston chambers 40 and 42 are sized to provide appropriate space for the pistons 26 and 28 to reciprocate. The seals associated with the pistons 26 and 28 maintain centering of the piston rod 30 and pistons 26 and 28 with reference to the piston chambers 40 and 42. Thus there is no "wobble," and accordingly no particular limitation on piston stroke.

The piston chamber 40 has an inlet port 44 and an outlet port 46 within the body 22, with respective check valves 48 and 50 associated the ports 44 and 46. Likewise, the piston chamber 42 has an inlet port 52 and an outlet port 54 within the body 22, with respective check valves 56 and 58 within the ports 52 and 54. Externally the two inlet ports 44 and 52 may or may not be connected together in a "Y" junction (not shown), and the two outlet ports 46 and 54 may or may not be connected together in another "Y" junction (not shown). During operation, as the pistons 26 and 28 reciprocate, flow of fluid from the two inlet ports 44 and 52 through the piston chambers 40 and 42 of the pump or compressor 20 to the two outlet ports 46 and 54 is essentially continuous, with minimal pulsation.

Although the compressor 20 includes a single pair 24 of pistons 26 and 28 and a single piston rod 30, as described hereinbelow with reference to FIGS. 10-14 compressors embodying the invention may also have multiple pairs of pistons and corresponding multiple piston rods. Accordingly, the piston rod 30 may also be termed a first piston rod 30.

In the pump or compressor 20 of FIGS. 1-3, the piston chambers 40 and 42 are stationary. The piston rod 30, the pistons 26 and 28, and the piston chambers 40 and 42 are non-rotating. The piston rod 30, as well as the pistons 26 and 28 reciprocate.

The materials used in the pump or compressor 20 may include Teflon® or Rulon® PTFE plastic piston heads or seals 32 and 34 or other slippery, low friction piston seals which are self-entering and floating and maintain the alignment of the pistons 24 and 26. Seals may face either way. The body 22 of the compressor 20, the piston rod 30, the pistons 26 and 28, and the piston chambers 40 and 42 may be made of durable materials, such as low carbon steel, aluminum, and even polymeric materials. Appropriate materials are selected for both the compressor and the associated seals to minimize or at least control thermal expansion of the components during use.

A driven rotatable shaft 66 is connected to a power source delivering rotational energy in a conventional manner. In the orientations of FIGS. 1 and 3 the driven rotatable shaft 66 extends through the compressor 20 in a vertical orientation. Typically, a motor (not shown) drives the rotatable shaft 66.

The rotatable shaft 66 is connected to and drives a circular eccentric 70, which is off center with reference to the rotatable shaft 66. In other words, the center of the eccentric 70 is not on the axis of the rotatable shaft 66. (Although not specifically illustrated, in order to minimize vibration, the eccentric 70 may be weighted so that its mass is balanced with reference to the rotatable shaft 66.) The terminology "eccentric" or "off-center" means simply that the center of the eccentric 70 is not on the axis of the rotatable shaft 66.

The connection and driving may be accomplished in a variety of ways. In the illustrated embodiment, the shaft 66 is keyed, and thus includes a slot 72. A corresponding slot 74 is provide in the circular eccentric 70, and a key 76 is inserted in the slots 72 and 74. Accordingly, the eccentric 70 is rotationally fixed to the shaft 66.

An outer circular ring 82 surrounds and is connected to the circular eccentric 70 via a bearing 84. Accordingly, the eccentric 70 can rotate while the outer circular ring 82 does not, or vice versa, depending on the particular embodiment. In the illustrated embodiment, the bearing 84 is a needle roller bearing 84. A ball bearing may as well be employed.

A drive pin 86 engages the outer circular ring 82 at a fixed position on the circular ring 82, and also engages the piston rod 30. There is some relative rotation, so there is a bearing at one end of the drive pin 86. In the illustrated embodiment, a bearing 87 is provided where the drive pin 86 engages the piston rod 30. Alternatively a bearing may be provided where the drive pin 86 engages the outer circular ring 82. The piston rod 30 has a slotted opening 88 through which the rotatable shaft 66 extends.

As a result, when rotational motion of the shaft 66 rotates the circular eccentric 70, the drive pin 86 and the piston rod 28 move back and forth relative to the rotatable shaft 66. In other words, the compressor 20 accommodates a sliding lateral movement of the piston rod 30. The pistons 26 and 28 are alternately closer to and farther from the rotatable shaft 66. Rotational movement of the driven shaft 66 is converted to reciprocating movement of the piston rod 30 and pistons 26 and 28 relative to the piston chambers 40 and 42.

An inner circular arrow 90 represents rotation of the shaft 66, and an outer circular arrow 92 represents rotation of the eccentric 70 driven by the shaft 66. Rotational direction is not relevant because check valves are employed. Each of the circular arrows 90 and 92 accordingly has a single arrow head. The pump or compressor 20 operates the same way in either rotational direction. "Input" and "output" are determined by the inlet check valves 48 and 56 and by the outlet check valves 50 and 58.

As noted above, in the compressor 20 embodiment of FIGS. 1-3, the piston chambers 40 and 42 are stationary. The piston rod 30, as well as the single pair 24 of pistons 26 and 28, reciprocate relative to the piston chambers 40 and 42, but do not otherwise move. In addition, the eccentric 70 rotates.

Figure 4:
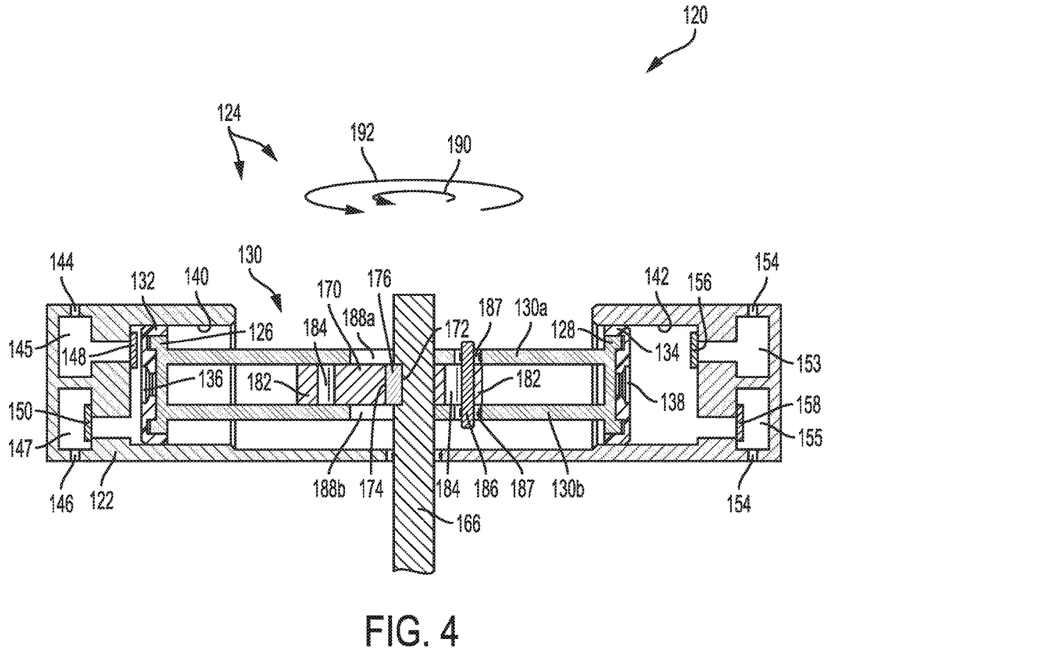
FIG. 4 is a sectional front sectional view of a second pump or compressor embodying the invention, in the same orientation as FIG. 1.

Referring next to FIG. 4, illustrated as a representation and somewhat schematically is a second pump or compressor 120 embodying the invention. The second pump or compressor 120 of FIG. 4 is similar to the first pump or compressor 20 of FIGS. 1-3, but differs in the location of the eccentric, and the associated drive pin. Also, the check valves are shown as flapper valves.

More particularly, the pump or compressor 120 has a body generally designated 122, and includes a single pair 124 of pistons 126 and 128, which preferably are rectangular but which may be circular in cross section. The pistons 126 and 128 are attached at opposite ends of a piston rod 130. The pistons 126 and 128 have respective representative piston heads or seals 132 and 134. The piston heads or seals 132 and 314 provide sealing and centering and, in the illustrated embodiment are made of a polytetrafluoroethylene (PTFE) plastic material such as Teflon® or Rulon®. The piston heads 132 and 134 are secured by machine screws 316 and 138. Again, it will be appreciated that the illustrated construction is representative only, and that various forms of seals and seal mountings may be employed. What is important is that the seals extend radially beyond the pistons 126 and 128.

The piston rod 130 again is unitary. In other words, the piston rod 130 is continuous along its length between the pistons 126 and 128. In addition, the piston rod 130 has no bearings or other support, other than by the pistons 126 and 128 (more particularly by the piston heads or seals 132 and 134). However, in the embodiment of FIG. 4 the piston rod 130 is split into two parts 130a and 130b. In the orientation of FIG. 4 these are an upper piston rod part 130a and a lower piston rod part 130b. The piston rod parts 130a and 130b may be a single piece, or two pieces attached to the piston heads 132 and 134 by threaded connections.

The pistons 126 and 128 reciprocate within respective individual piston chambers 140 and 142. The piston chambers 140 and 142 are sized to provide appropriate space for the pistons 126 and 128 to reciprocate.

The piston chamber 140 has an inlet port 144 communicating with an inlet port chamber 145, and an outlet port 146 communicating with an outlet port chamber 147. Respective check valves 148 and 150 in the form of flapper valves 148 and 150 control gas flow between the piston chamber 140 and the two port chambers 145 and 147.

Likewise, the piston chamber 142 has an inlet port 152 communicating with an inlet port chamber 153 and an outlet port 154 communicating with an outlet port chamber 155. Respective check valves 156 and 158 in the form of flapper valves 156 and 158 control gas flow between the piston chamber 142 and the two port chambers 153 and 155.

Externally the two inlet ports 144 and 152 may or may not be connected together in a "Y" junction (not shown), and the two outlet ports 146 and 154 may or may not be connected together in another "Y" junction (not shown). During operation, as the pistons 126 and 128 reciprocate, flow of fluid from the two inlet ports 144 and 152 through the piston chambers 140 and 142 of the pump or compressor 120 to the two outlet ports 146 and 154 is essentially continuous, with minimal pulsation.

A driven rotatable shaft 166 is connected to a power source delivering rotational energy in a conventional manner. In the orientation of FIG. 4 the driven rotatable shaft 166 extends through the compressor 120 in a vertical orientation. Typically, a motor (not shown) drives the rotatable shaft 166.

The rotatable shaft 166 is connected to and drives a circular eccentric 170, which is off center with reference to the rotatable shaft 166. In other words, the center of the eccentric 170 is not on the axis of the rotatable shaft 166. (Although not specifically illustrated, in order to minimize vibration, the eccentric 170 may be weighted so that its mass is balanced with reference to the rotatable shaft 166.)

In the embodiment of FIG. 4, the circular eccentric 170 is between the two parts 130a and 130b of the piston rod 130.

The connection and driving may be accomplished in a variety of ways. In the illustrated embodiment, the shaft 166 is keyed, and thus includes a slot 172. A corresponding slot 174 is provided in the circular eccentric 170, and a key 176 is inserted in the slots 172 and 174. Accordingly, the eccentric 170 is rotationally fixed to the shaft 166.

An outer circular ring 182 surrounds and is connected to the circular eccentric 170 via a bearing 184. Accordingly, the eccentric 170 can rotate while the outer circular ring 182 does not. In the illustrated embodiment, the bearing 184 again is a needle roller bearing 184. A ball bearing may as well be employed.

A drive pin 186 engages the outer circular ring 182 at a fixed position on the circular ring 182, and also engages both parts 130a and 130b of the piston rod 130 via bearings 187 in the piston rod parts 130a and 130b. The piston rod parts 130a and 130b have respective a slotted openings 188a and 188b through which the rotatable shaft 166 extends.

As a result, when rotational motion of the shaft 166 rotates the circular eccentric 170, the drive pin 186 and the piston rod 128 move back and forth relative to the rotatable shaft 166. Rotational movement of the driven shaft 166 is converted to reciprocating movement of the two parts 130a and 130b of the piston rod 130 and pistons 126 and 128 relative to the piston chambers 140 and 142.

An inner circular arrow 190 represents rotation of the shaft 166, and an outer circular arrow 192 represents rotation of the eccentric 170 driven by the shaft 166. Rotational direction is not relevant because check valves are employed.

Again, in the compressor 120 embodiment of FIG. 4, the piston chambers 140 and 142 are stationary. The two parts 130a and 130b of the piston rod 130, as well as the single pair 124 of pistons 126 and 128, reciprocate relative to the piston chambers 140 and 142, but do not otherwise move. In addition, the eccentric 170 rotates.

However, in the embodiment of FIGS. 5-7 described next below, piston chambers, pistons, and a piston rod all rotate, while the circular eccentric remains stationary. The pistons still reciprocate relative to and within the piston chambers.

In particular, with reference to FIGS. 5-7, illustrated again as a representation and somewhat schematically is a third pump or compressor 220 embodying the invention. As in the first pump or compressor 20 described hereinabove with reference to FIGS. 1-3 and the second pump or compressor 120 described hereinabove with reference to FIG. 4, the third pump or compressor 220 of FIGS. 5-7 has a body generally designated 222, and includes a single pair 224 of pistons 226 and 228. The pistons 226 and 228 are attached at opposite ends of a piston rod 230. The pistons 226 and 228 again have respective piston heads or seals 232 and 234. The piston heads 232 and 234 provide sealing and centering and, in the illustrated embodiment, are made of a PTFE plastic such as Teflon® or Rulon®. In the illustrated embodiment the piston heads 232 and 234 are secured by machine screws 236 and 238. Other forms of attachment may as well be employed, such as flat round washers (not shown) and screws.

The piston rod 230 again is unitary. In other words, the piston rod 230 is a single, continuous piece along its length between the pistons 226 and 228. In addition, the piston rod 230 has no bearings or other support, other than by the pistons 226 and 228 (more particularly by the piston heads 232 and 234).

The pistons 226 and 228 reciprocate within respective individual piston chambers 240 and 242.

Figure 5:
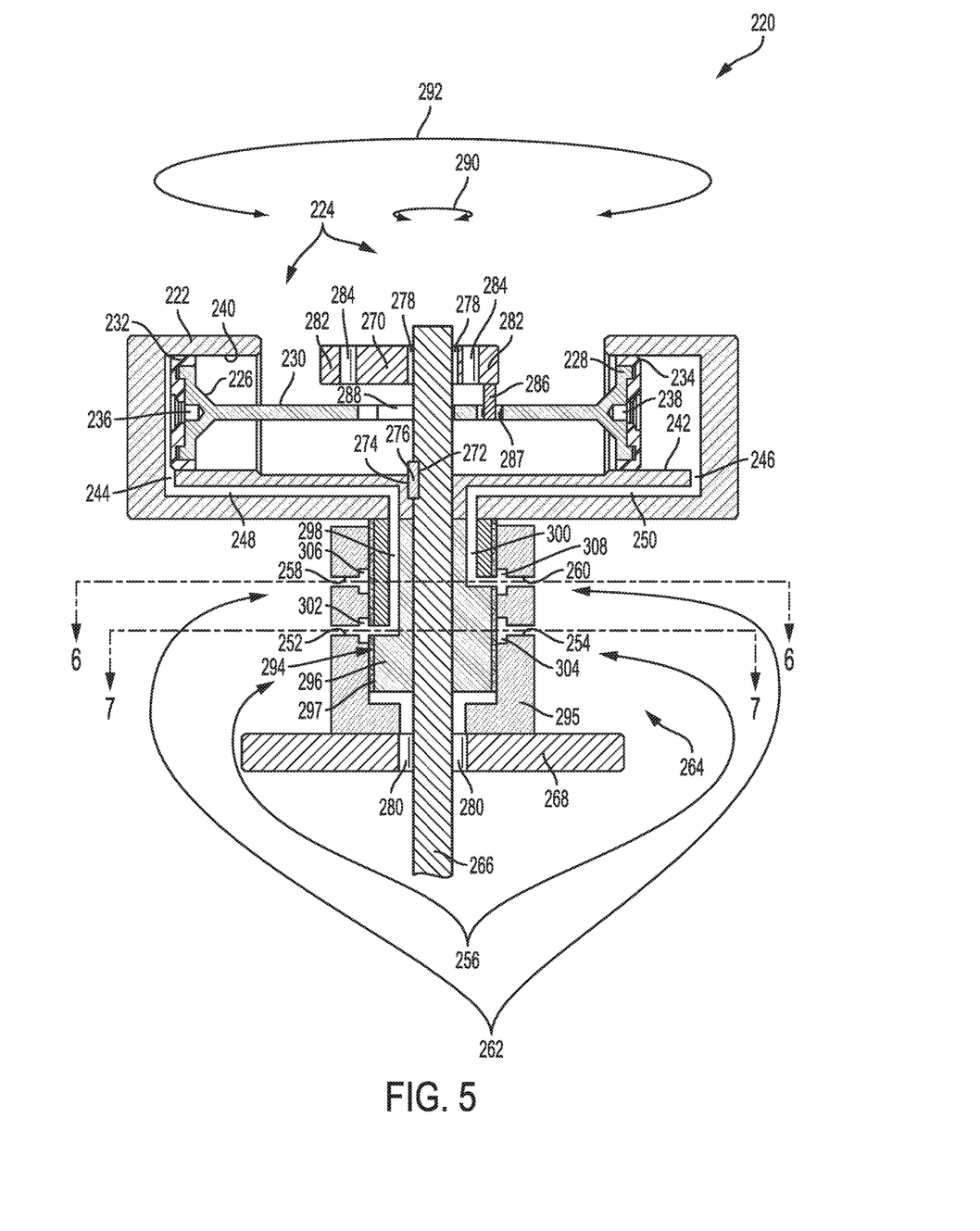
FIG. 5 is a sectional front sectional view of a third pump or compressor embodying the invention, in the same orientation as FIG. 1.
Figure 6:
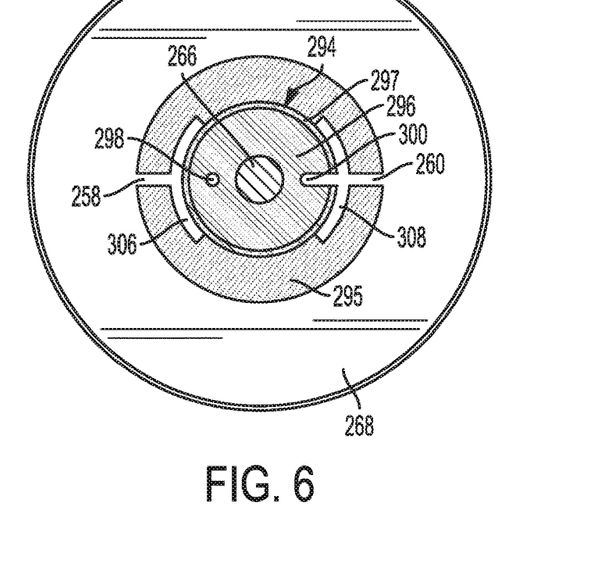
FIG. 6 is a cross sectional view taken on line 6-6 of FIG. 5.
Figure 7:
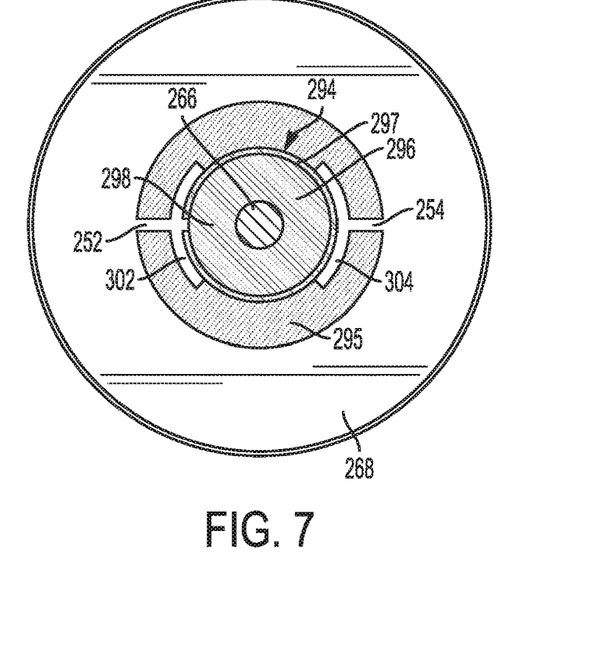
FIG. 7 is a cross sectional view taken on line 7-7 of FIG. 5.

Rather than the check valves 48, 46 and 50, 58 of the first compressor 20 of FIGS. 1-3, or the check valves 148, 146 and 150, 158 of the second compressor 120 of FIG. 4, the third compressor embodiment 220 of FIGS. 5-7 has a pair of ports 244 and 246 and corresponding passageways 248 and 250 within the body 222, in communication with respective piston chambers 240 and 242. The passageways 248 and 250 ultimately are connected alternately to ports 252 and 254 of a first pair 256 (lower ports) and alternately to ports 258 and 260 of a second pair 262 (upper pair), which are part of a rotary valve assembly 264 described hereinbelow.

As in the compressors 20 and 120, in the third compressor 220 of FIGS. 5-7 a driven rotatable shaft 266 is connected to a power source delivering rotational energy in a conventional manner. In the orientation of FIG. 4 the driven rotatable shaft 266 extends through the compressor 220 in a vertical orientation. Typically, a motor (not shown) drives the rotatable shaft 266. The compressor 220 includes a representative base end plate 268 through which the rotatable shaft 266 extends.

In the compressor 220 of FIGS. 5-7 the rotatable shaft 266 is connected to and drives the compressor 220 body 222, and therefore the piston chambers 240 and 242, the pistons 226 and 228, and the piston rod 230, while a circular eccentric 270 remains stationary. (The mechanical structure for supporting and keeping the eccentric 270 stationary is not shown in the representation of FIGS. 5-7.) As in the compressor 20 of FIGS. 1-3 and the compressor 120 of FIG. 4, in the compressor 220 of FIGS. 5-7 the eccentric 270 is off center with reference to the rotatable shaft 266. The driving and connection may be accomplished in a variety of ways. In the illustrated embodiment, the shaft 266 is keyed, and thus includes a slot 272. There is a corresponding slot 274 in the compressor 220 body 222, and a key 276 is inserted in the slots 272 and 274. A needle roller bearing 278 for the shaft 266 is provided in the eccentric 270 so that the shaft 266 can rotate while the eccentric 270 remains stationary. Another needle roller bearing 280 for the shaft 266 is provided in the base end plate 268, which is stationary.

An outer circular ring 282 surrounds and is connected to the circular eccentric 270 via a needle roller bearing 284, as an example. Accordingly, the outer circular ring 282 can rotate with the piston chambers 240 and 242, the pistons 226 and 228, and the piston rod 230, while the eccentric 270 does not rotate.

A drive pin 286 engages the outer circular ring 282 at a fixed position on the circular ring 282, and also engages the piston rod 230. There is a bearing 287 where the drive pin 286 engages the piston rod 230. The piston rod 230 has a slotted opening 282 through which the rotatable shaft 266 extends.

As a result, when rotational motion of the shaft 266 rotates the piston chambers 240 and 242, the pistons 226 and 228, and the piston rod 230 with the attached drive pin 286, the drive pin 286 and the piston rod 230 move back and forth relative to the rotatable shaft 166. The pistons 226 and 228 are alternately closer to and farther from the rotatable shaft 266. Rotational movement of the driven shaft 260 is converted to reciprocating movement of the piston rod 230 and pistons 226 and 228 relative to the piston chambers 240 and 242.

In the third compressor 220 of FIGS. 5-7, an inner circular arrow 290 represents rotation of the shaft 266, and an outer circular arrow 292 represents rotation of the piston chambers 240 and 242, the pistons 226 and 228, and the piston rod 230 with the attached drive pin 286, all driven by the shaft 266. Rotational direction determines "input" and "output" as described next below in the context of the rotary valve assembly 264. Each of the circular arrows 290 and 292 accordingly has two arrow heads.

The rotary valve assembly 264 includes a valve body 294 and a port body 295. The valve body 294 takes the general form of a solid cylinder. The valve body 294 is fixed to and rotates with the compressor 220 body 222 (along with rotation of the piston chambers 240 and 242, the pistons 226 and 228, and the piston rod 230). The port body 295 takes the general form of a hollow cylinder, which fits around the valve body 294. The port body 295 is stationary. In the illustrated embodiment, the port body 295 is fixed to the base end plate 268.

The valve body 294 has an inner structural steel portion 296, and an outer layer 297 made of carbon, which is machined. The port body 295 may be made of steel, and likewise is machined at least on its inner surface. The valve body 294 and port body 295 are machined to close tolerances such that the valve body 294 can rotate within the port body 295, while at the same time there is minimal gas leakage.

The first pair 256 of ports 252 and 254 (lower pair) are part of the port body 295. The first pair 256 of ports 252 and 254 may be simple drilled apertures, preferably at least partially threaded, with suitable fittings (not shown). Externally the ports 252 and 254 may or may not be connected together in a "Y" junction (not shown). The second pair 262 of ports 258 and 260 (upper pair) likewise are part of the port body 196, and also may be simple drilled apertures, preferably at least partially threaded, with suitable fittings (not shown). The ports 258 and 262 may or may not be connected together in another "Y" junction (not shown). In the third compressor 220 embodiment of FIGS. 5-7 the ports of the first pair 256 and of the second pair 262 are not labeled "input" and "output" because input and output depend on the direction of rotation.

Within the valve body 294 is a first passageway 298 which directly communicates with the passageway 248 in the body 222 connected to the piston chamber 240. A second passageway 300 directly communicates with the passageway 250 in the body 222 connected to the piston chamber 242.

Circumferential timing grooves are provided, and may be in either the rotating valve body 294 or the stationary port body 295. In the illustrated embodiment, lower circumferential grooves 302 and 304 are formed in the port body 295 in communication with the lower ports 252 and 254, respectively; and upper circumferential grooves 306 and 308 are formed in the port body 295 in communication with the ports 258 and 260, respectively. The lower circumferential grooves 302 and 304 are positioned so as to be in fluid communication with the passageway 298 (and thereby with the passageway 248), depending on rotational position. The upper circumferential grooves 306 and 308 are positioned so as to be in fluid communication with the passageway 300 (and thereby with the passageway 250), again depending on rotational position.

The circumferential groves 302, 304, 306 and 308 establish what may be viewed as the timing of the rotary valve assembly 264, in other words at which rotational positions the piston chamber 240 is in communication with the port 252 or the port 254, and at which rotational positions the piston chamber 242 is in communication with the port 258 or the port 260. The circumferential groves 302, 304, 306 and 308 are each less than 180° in circumferential extent. As noted above, although in the illustrated embodiment the circumferential groves 302, 304, 306 and 308 are in the port body 295, the circumferential groves 302, 304, 306 and 308 may as well be in the valve body 294.

During operation, the rotatable shaft 266 is rotated in either a forward or reverse direction, and the rotational direction determines which of the port pairs 256 and 262 is a fluid "input" and which is a fluid "output."

In the first compressor 20 embodiment of FIGS. 1-3, the second compressor embodiment 120 of FIG. 4, and the third compressor embodiment 220 of FIGS. 5-7, during operation when the shaft 66, 166 or 266 is rotated, the pistons 26 and 28; or 126 and 128; or 225 and 228 are alternately closer to and farther from the rotatable shaft 66, 166, or 266. Rotational movement of the shaft 66, 166, or 266 is converted to reciprocating movement of the piston rod 30, 130 or 230 and pistons 26 and 28, 126 and 128, or 226 and 228 relative to the piston chambers 40 and 42, 140 and 142, or 240 and 242 by the disclosed mechanisms which include the circular eccentric 70, 170 or 270, the outer circular ring 82, 182 or 282, and the drive pin 86, 186 or 286.

Fluid is pumped out of the piston chamber 40, 140 or 240 as the piston 26, 126 or 226 moves into the piston chamber 40, 140 or 240. Conversely, fluid is drawn into the piston chamber 40, 140 or 240 as the piston 26, 126 or 226 moves out of the piston chamber 40, 140 or 240. Similar fluid pumping occurs with reference to the piston chamber 42, 142 or 242.

Considering the piston chamber 40, 140 or 240, in the first compressor 20 embodiment of FIGS. 1-3, as the piston 26 moves into the piston chamber 40, fluid exits through the check valve 50 and outlet port 46. Likewise, in the second compressor 120 embodiment of FIG. 4, as the piston 126 moves into the piston chamber 140, fluid exits through the check valve 150 and outlet port 146. In the third compressor embodiment 220 of FIGS. 5-7, fluid exits through either the port 252 or the port 254 of the rotary valve assembly 264. Conversely, fluid is drawn into the piston chamber 40, 140 or 240 as the piston 26, 126 or 226 moves out of the piston chamber 40, 140 or 240. In the first compressor 20 embodiment of FIGS. 1-3 fluid enters through the check valve 48 and inlet port 44. In the second compressor 120 embodiment of FIG. 4 fluid enters through the check valve 148 and inlet port 144. In the third compressor embodiment 220 of FIGS. 5-8, fluid enters through either the port 252 or the port 254 of the rotary valve assembly 264.

Considering the piston chamber 42, 142 or 242 in the first compressor 20 embodiment of FIGS. 1-3, as the piston 28 moves into the piston chamber 42, fluid exits through the check valve 58 and outlet port 56. In the second compressor 120 embodiment of FIG. 4, as the piston 128 moves into the piston chamber 142, fluid exits through the check valve 158 and outlet port 156. In the third compressor embodiment 220 of FIGS. 5-7, fluid exits through either the port 256 or the port 260 of the rotary valve assembly 254. Conversely, fluid is drawn into the piston chamber 42, 142 or 242 as the piston 28, 128 or 228 moves out of the piston chamber 42, 142 or 242. In the first compressor 20 embodiment of FIGS. 1-3 fluid enters through the check valve 56 and inlet port 54. In the second compressor 120 embodiment of FIG. 4 fluid enters through the check valve 156 and inlet port 152. In the third compressor embodiment 220 of FIGS. 5-8, fluid enters through either the port 256 of the port 260 of the rotary valve assembly 254.

Again, depending upon the embodiment the rotatable shaft 66, 166 or 266 may be connected to drive either the eccentric 70 or 170 in rotation; or the compressor body 222 (and thereby the piston chambers 240 and 242, the pistons 226 and 228, and the piston rod 230) in rotation.

Figure 8:
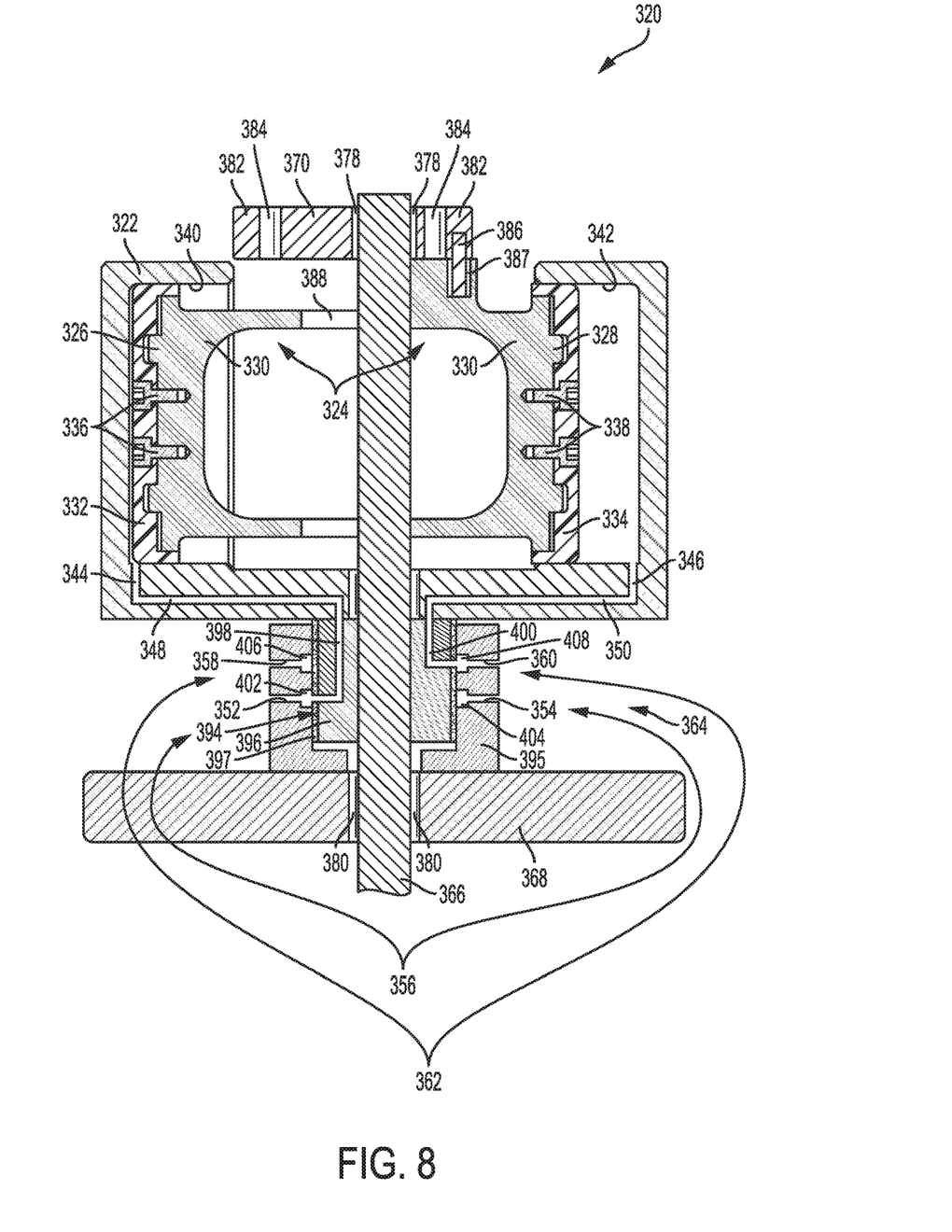
FIG. 8 is a sectional front sectional view of a fourth pump or compressor embodying the invention.

With reference now to FIG. 8, disclosed is a fourth pump or compressor 320 embodiment which is like the compressor 220 embodiment of FIGS. 5-7, except more compact. In the embodiment of FIG. 8, again the piston chambers, the pistons, and the piston rod all rotate, while the circular eccentric remains stationary. The pistons reciprocate relative to and within the piston chambers.

Briefly, with reference to FIG. 8 the fourth pump or compressor 320 embodying the invention has a body generally designated 322, and includes a single pair 324 of pistons 326 and 326. The pistons 326 and 328 are attached at opposite ends of a unitary piston rod 330, which has no bearings or other support, other than by the pistons 326 and 328. The pistons 326 and 328 have respective piston heads 332 and 334 which provide sealing and centering. In the illustrated embodiment, the piston heads 332 and 334 are secured by machine screws 336 and 338. The pistons 326 and 328 reciprocate within respective individual piston chambers 340 and 342.

A pair of ports 344 and 346 and corresponding passageways 348 and 350 are formed within the body 322, in communication with respective piston chambers 340 and 342. The passageways 348 and 350 ultimately are connected alternately to ports 353 and 354 of a first pair 256 (lower ports) and alternately to ports 358 and 360 of a second pair 262 (upper pair), which are part of a rotary valve assembly 364.

A driven rotatable shaft 366 is connected to a power source delivering rotational energy. Typically, a motor (not shown) drives the rotatable shaft 366 which extends through a base end plate 368.

The rotatable shaft 366 is connected to and drives the compressor 320 body, and therefore the piston chambers 340 and 342, the pistons 326 and 328, and the piston rod 330, while a circular eccentric 370 remains stationary. The eccentric 370 is off center with reference to the rotatable shaft 366. The shaft 366 is keyed, and thus includes a slot 372. A corresponding slot 374 is provided in the compressor 320 body 322, and a key 376 is inserted in the slots 372 and 374. A needle roller bearing 378 for the shaft 366 is provided in the eccentric 370 so that the shaft 366 can rotate while the eccentric 370 remains stationary. Another needle roller bearing 380 for the shaft 366 is provided in the base end plate 368, which is stationary.

An outer circular ring 382 surrounds and is connected to the circular eccentric 370 via a needle roller bearing 384. Accordingly, the outer circular ring 382 can rotate with the piston chambers 340 and 342, the pistons 326 and 328, and the piston rod 330, while the eccentric 370 does not rotate.

A drive pin 386 engages the outer circular ring 382 at a fixed position on the circular ring 382, and also engages the piston rod 330. A bearing 387 is provided where the drive pin 386 engages the piston rod 330. The piston rod 330 has an opening 382 through which the rotatable shaft 366 extends.

The rotary valve assembly 364 includes a valve body 394 and a port body 395. The valve body 394 takes the general form of a solid cylinder. In the compressor 320 embodiment of FIG. 8 the valve body 394 rotates with the compressor 320 body 322 (along with rotation of the piston chambers 340 and 342, the pistons 326 and 328, and the piston rod 330). The port body 395 takes the general form of a hollow cylinder, which fits around the valve body 394. The port body 395 is stationary. In the illustrated embodiment, the port body 395 is fixed to the base end plate 368. The valve body 394 has an inner structural steel portion 396, and an outer layer 397 made of carbon, which is machined.

Still referring to FIG. 8, the first pair 356 of ports 352 and 354 (lower pair) are part of the port body 395, and may be simple drilled apertures, at least partially threaded, with suitable fittings (not shown). Externally the ports 352 and 354 may or may not be connected together in a "Y" junction (not shown). The second pair 362 of ports 358 and 360 (upper pair) likewise are part of the port body 395, and also may be simple drilled apertures, preferably at least partially threaded, with suitable fittings (not shown). The ports 358 and 360 may or may not be connected together in another "Y" junction (not shown).

Within the valve body 394 is a first passageway 398 which directly communicates with the passageway 348 in the body 322 connected to the piston chamber 340. A second passageway 400 directly communicates with the passageway 350 in the body 322 connected to the piston chamber 340. Circumferential timing grooves are provided, and again may be in either the rotating valve body 394 or the stationary port body 395. In the illustrated embodiment, lower circumferential grooves 402 and 404 are formed in the port body 395 in communication with the lower ports 352 and 354, respectively; and upper circumferential grooves 406 and 408 are formed in the port body 395 in communication with the ports 358 and 360, respectively. The lower circumferential grooves 402 and 404 are positioned so as to be in fluid communication with the passageway 398 (and thereby with the passageway 348), depending on rotational position. The upper circumferential grooves 406 and 408 are positioned so at to be in fluid communication with the passageway 400 (and thereby with the passageway 350), again depending on rotational position.

Figure 9:
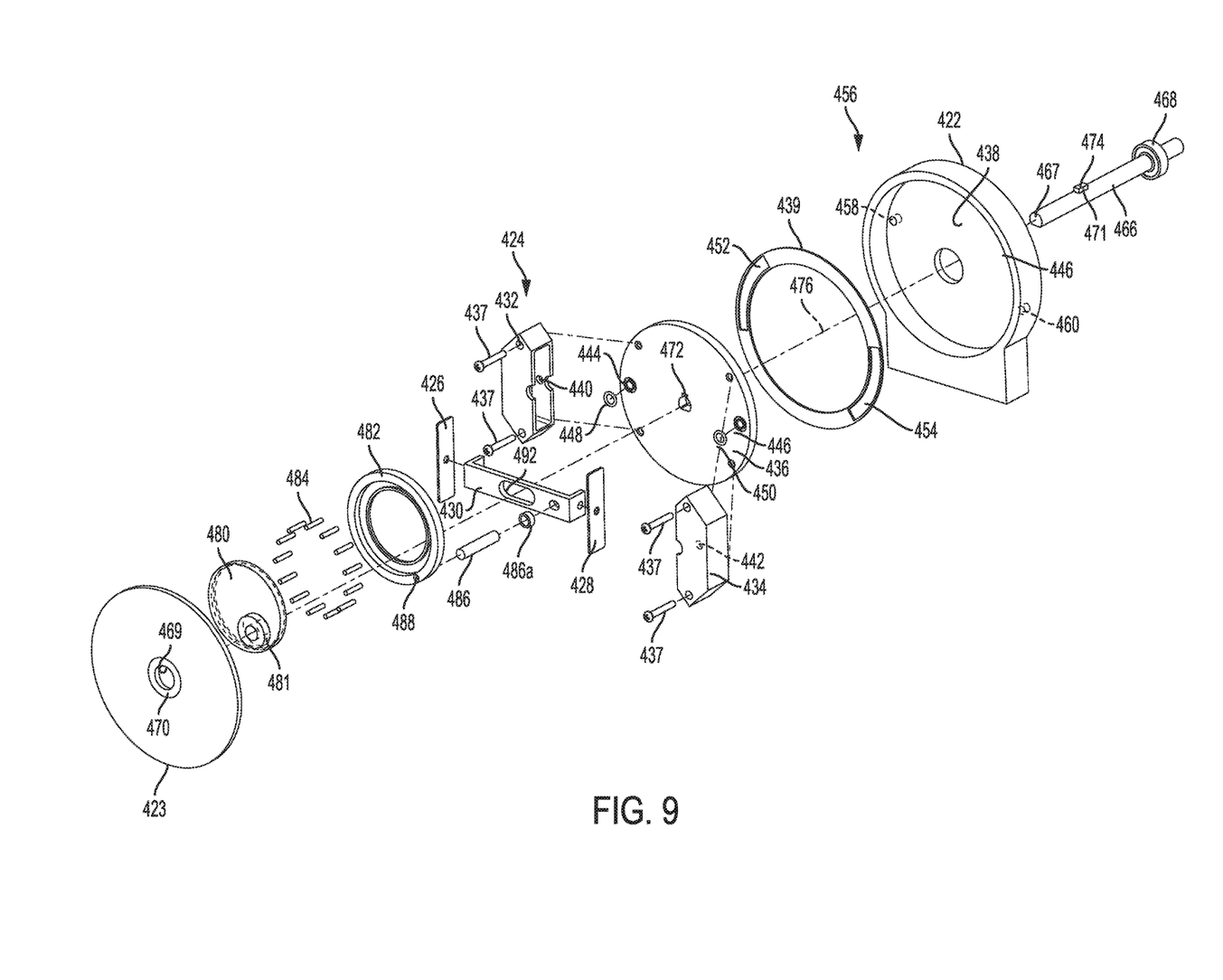
FIG. 9 is an exploded view of a fifth pump or compressor embodying the invention.

Referring now to FIG. 9, disclosed as an exploded view is a fifth pump or compressor 420 embodiment which is based on the third compressor 220 embodiment of FIGS. 5-7. In the embodiment of FIG. 9, again the piston chambers, the pistons, and the piston rod all rotate, while the circular eccentric remains stationary. The pistons reciprocate relative to the piston chambers.

Briefly, with reference to FIG. 9 the fifth pump or compressor 420 embodying the invention has a pair of stationary end pieces 422 and 423, and includes a single pair 424 of pistons 426 and 426, which take the form of flat plates. The pistons 426 and 428 are attached at opposite ends of a unitary piston rod 430, which has no bearings or other support, other than by the pistons 426 and 428. The pistons 426 and 428 reciprocate within respective individual piston chambers 432 and 434, which are secured to a rotatable plate 436 by machine screws 437. The pistons 426 and 428 also have respective piston heads or seals, which are omitted from FIG. 9 for clarity of illustration. The rotatable plate 436 is received within a cavity 438 in the stationary end piece 422 (right side in the orientation of FIG. 9), and there is a non-rotating circular carbon gasket 439 in between the rotatable plate 436 and the stationary end piece 422. A spring (not shown) may be employed to press the rotatable plate 436 against the carbon gasket 439 and against the end piece 422.

The piston chambers 432 and 434 have respective ports 440 and 442, which take the form of simple apertures, in alignment with respective corresponding ports or apertures 444 and 446 in the rotatable plate 436. Rubber "O" rings 448 and 450 may be employed to provide sealing. The ports or apertures 444 and 446 in the rotatable plate 436 communicate with circumferential channels 452 and 454 in the carbon gasket 439, forming a rotary valve 456. Ports 458 and 460 (shown in dash lines) are formed in the stationary end piece 422 in fluid communication with respective circumferential channels 452 and 454.

A driven rotatable shaft 466 having a distal end 467 is connected to a power source delivering rotational energy. Typically, a motor (not shown) drives the rotatable shaft 466. The rotatable shaft 466 extends through the stationary end plate 422, supported by a bearing 468, and drives the rotatable plate 436 in rotation. The bearing 468 may be a roller bearing, which fits within a recess (not shown) within the end piece 422. The distal end 467 of the shaft 466 extends though an aperture 469 in the stationary end piece 423, with another roller bearing 470. The shaft 466 is keyed, and thus includes a slot 471. A corresponding slot 472 is provided in the rotatable plate 436, and a key 474 is inserted in the slots 471 and 472. The rotatable shaft 466 may be viewed as establishing a centerline 476 of the compressor 420, which centerline 476 is represented by an axis 476 in the exploded view of FIG. 9.

By driving the rotatable plate 436, the rotatable shaft 466 also drives the piston chambers 440 and 442, the pistons 426 and 428, and the piston rod 430 in rotation.

Mounted to the stationary end piece 423 (left side in the orientation of FIG. 9) is a fixed circular eccentric 480 which is off-center with reference to the axis 476. The circular eccentric 480 has an apertured pedestal 481 and is stationary during operation.

An outer circular ring 482 surrounds and is connected to the circular eccentric 480 via a needle roller bearing 484. Accordingly, the outer circular ring 482 can rotate with the piston chambers 440 and 442, the pistons 426 and 428, and the piston rod 430, while the eccentric 480 does not rotate.

A drive pin 486 engages the outer circular ring 482 at a fixed position 488 on the circular ring 482, and also engages the piston rod 430. A bearing 486*a* is provided where the drive pin 486 engages the piston rod. To accommodate reciprocation of the piston rod 430, the piston rod 430 has a slotted opening 492 through which the rotatable shaft 466 extends.

Figure 10:
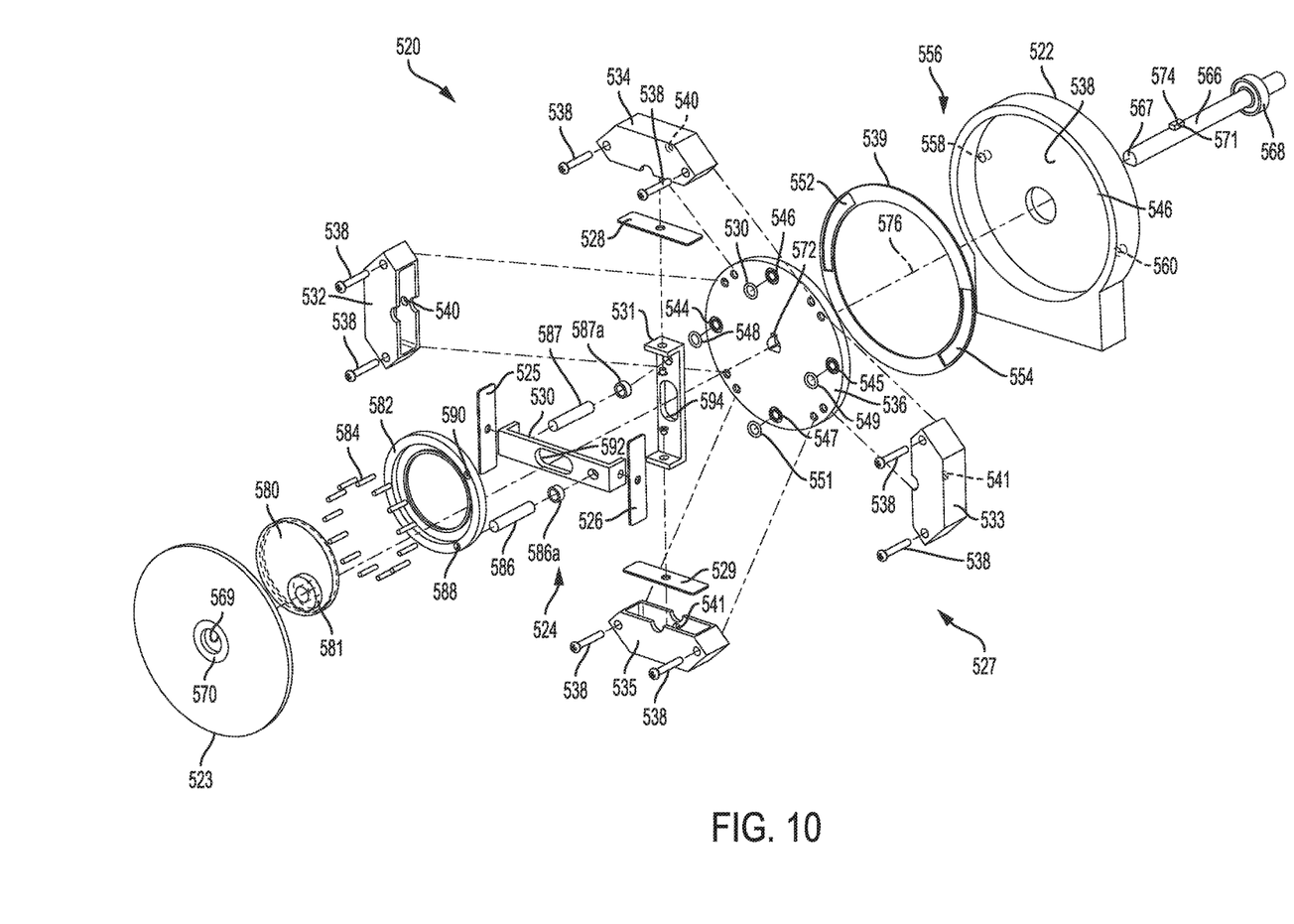
FIG. 10 is an exploded view of a sixth pump or compressor embodying the invention, employing two piston pairs.
Figure 11:
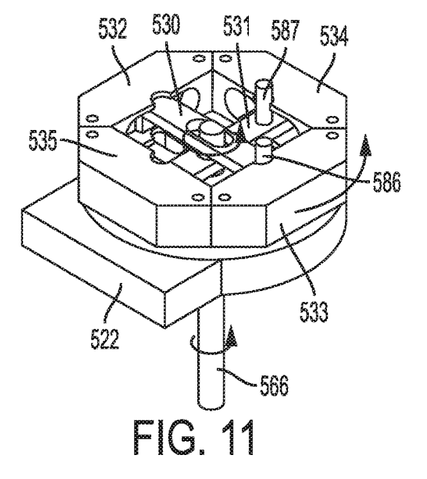
FIG. 11 is generally a three dimensional view of the pump or compressor of FIG. 10 as assembled, but omitting the eccentric and end piece (top end piece in the orientation of FIG. 11) so as to show piston rods inside.
Figure 12:
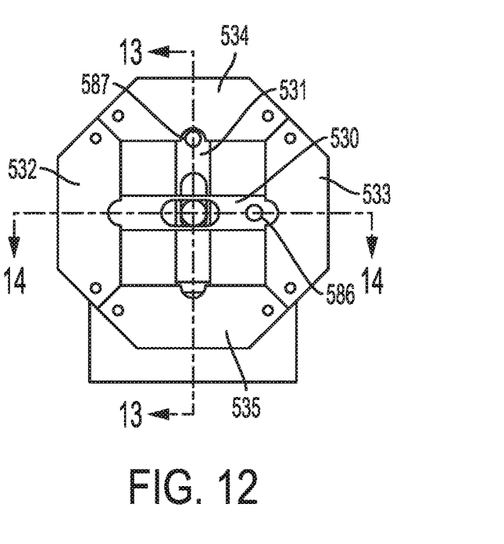
FIG. 12 is generally a top view of the sixth pump or compressor of FIG. 10, but also omitting the eccentric and end piece (top end piece in the orientation of FIG. 12) so as to show piston rods inside.
Figure 13:
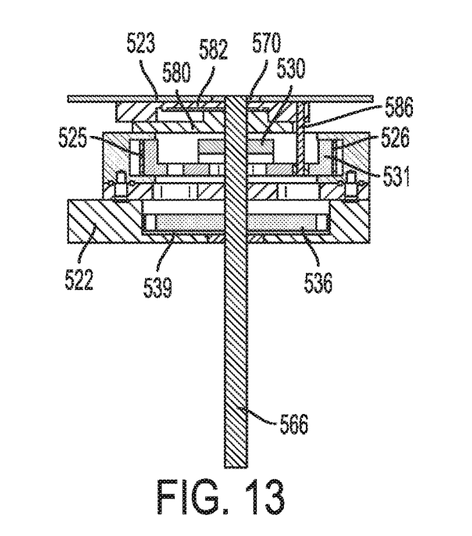
FIG. 13 is a side cross-sectional view of the sixth pump or compressor of FIG. 10, generally taken along line 13-13 of FIG. 12, but including the eccentric and end piece.
Figure 14:
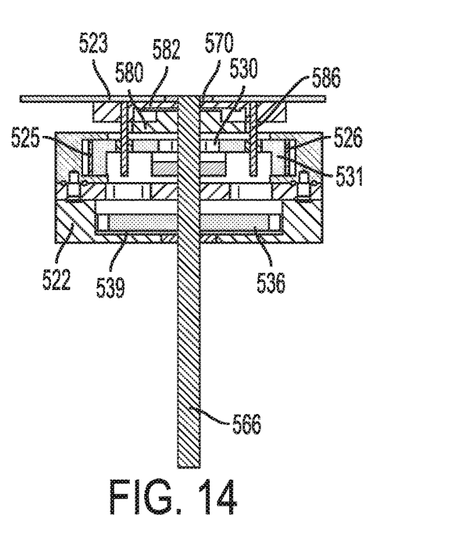
FIG. 14 is another side cross-sectional view of the sixth pump or compressor of FIG. 10, taken along line 14-14 of FIG. 12, but also including the eccentric and end piece.

Referring finally to FIGS. 10-14, disclosed is a sixth pump or compressor 520 embodiment. The pump or compressor 520 differs from the pumps or compressors described hereinabove in that there are two pairs of pistons, rather that a single pair. In the embodiment of FIGS. 10-14, the piston chambers, the pistons, and the piston rod all rotate, while the circular eccentric remains stationary. However, the invention may as well be embodied in a pump or compressor in which the piston chambers, two piston pairs, and two piston rods are all non-rotating. Moreover, more than two pairs of pistons may be provided. FIG. 10 is similar to FIG. 9, except that there are two pairs of pistons in FIG. 10, but only one pair in FIG. 9.

Briefly, the sixth pump or compressor 520 of FIGS. 10-14 embodying the invention has a pair of stationary end pieces 522 and 423, and includes a first pair 524 of pistons 525 and 526, as well as a second pair 527 of pistons 528 and 529. The pistons 525, 526, 528 and 529 take the form of flat plates. The pistons 525 and 526 of the first pair 524 are attached at opposite ends of a first unitary piston rod 530, which has no bearings or other support, other than by the pistons 525 and 526. The pistons 528 and 529 of the second pair 527 are attached at opposite ends of a second unitary piston rod 531, which likewise has no bearings or other support, other than by the pistons 528 and 529. The pistons 525 and 526 reciprocate within respective individual piston chambers 532 and 533, and pistons 528 and 529 reciprocate within respective individual piston chambers 534 and 535. The piston rods 530 and 531 have an elongated (in width) "U" shape and face each other in a somewhat nested manner such that the pistons 525, 526, 528 and 529 are within the same plane, and the piston chambers 532, 533, 534 and 535 are also within that same plane; the entire structure is compact. The piston chambers 532, 533, 534 and 535 are secured to a rotatable plate 536 by machine screws 537. The pistons 525, 526, 528 and 529 have respective piston heads or seals (omitted from FIGS. 11-15 for clarity of illustration). The rotatable plate 536 is received within a cavity 538 in the stationary end piece 522 (right side in the orientation of FIG. 10), and there is a non rotating circular carbon gasket 539 in between the rotatable plate 536 and the stationary end piece 522. A spring (not shown) may be employed to press the rotatable plate 536 against the carbon gasket 539 and against the end piece 522.

The piston chambers 532 and 533 have respective ports 540 and 541, which take the form of simple apertures, in alignment with respective corresponding ports or apertures 544 and 545 in the rotatable plate 536. Likewise, the piston chambers 534 and 535 have respective ports 540 and 541, which take the form of simple apertures, in alignment with respective corresponding ports or apertures 546 and 547 in the rotatable plate 536. Rubber "0" rings 548, 549 and 550, 551 may be employed to provide sealing. The ports or apertures 544, 545, 546 and 547 in the rotatable plate 536 communicate with circumferential channels 552 and 554 in the carbon gasket 539, forming a rotary valve 556. Ports 558 and 560 (shown in dash lines) are formed in the stationary end piece 522 in fluid communication with respective circumferential channels 552 and 554.

A driven rotatable shaft 566 having a distal end 467 is connected to a power source delivering rotational energy. The rotatable shaft 566 extends through the stationary end plate 522, supported by a bearing 568, and drives the rotatable plate 536 in rotation. The bearing 568 may be a roller bearing, which fits within a recess (not shown) within the end piece 522. The distal end 567 of the shaft 566 extends though an aperture 569 in the stationary end piece 523, with another roller bearing 570. The shaft 566 is keyed, and thus includes a slot 571. A corresponding slot 572 is provided in the rotatable plate 536, and a key 574 is inserted in the slots 571 and 572. The rotatable shaft 566 may be viewed as establishing a centerline 576 of the compressor 520, which centerline 576 is represented by an axis 576 in the exploded view of FIG. 11.

By driving the rotatable plate 536, the rotatable shaft 566 also drives the piston chambers 532, 533 and 534, 535, the pistons 525, 526 and 528, 529, and the piston rods 530 and 531 in rotation.

Mounted to the stationary end piece 523 is a fixed circular eccentric 580 which is off-center with reference to the axis 578. The circular eccentric 580 has an apertured pedestal 581 and is stationary during operation.

An outer circular ring 582 surrounds and is connected to the circular eccentric 580 via a needle roller bearing 584. Accordingly, the outer circular ring 582 can rotate with the piston chambers 532, 533 and 534, 535, the pistons 525, 526 and 528, 529 and the piston rods 530 and 531, while the eccentric 580 does not rotate.

A first drive pin 586 engages the outer circular ring 582 at a fixed position 588 on the circular ring 582, and also engages the first piston rod 530. A bearing 586a is provided where the first drive pin 586 engages the first piston rod 530. Likewise, a second drive pin 587 engages the outer circular ring 582 at another fixed position 590 on the circular ring 482, and also engages the second piston rod 531. A bearing 587a is provided where the second drive pin 587 engages the second piston rod 531. To accommodate reciprocation of the first and second piston rods 531 and 532, the first piston rod 530 has a slotted opening 592 through which the rotatable shaft 566 extends, and the second piston rod 531 has a slotted opening 594 through which the rotatable shaft 566 extends.

While specific embodiments of the invention are illustrated and described herein, it is realized that numerous modifications and changes will occur to those skilled in the art. It is therefore to be understood that the appended claims are intended to cover all such modifications and changes that fall within the true spirit and scope of the invention.

What is claimed is:

1. A compressor comprising:
    a rotatable shaft;
    at least a first piston rod substantially perpendicular to said rotatable shaft and connecting a first pair of pistons at opposite ends of said piston rod, said piston rod moving back and forth relative to said rotatable shaft;
    a circular eccentric;
    a circular ring connected to said circular eccentric via a bearing; and
    a drive pin engaging said circular ring at a fixed position on said circular ring and engaging said at least a first piston rod such that, when rotational motion of the shaft rotates either said first piston rod and first pair of pistons or said circular eccentric, said drive pin and said first piston rod move back and forth relative to said rotatable shaft.

2. A compressor according to claim 1, wherein said at least a first piston rod defines an opening through which said rotatable shaft extends.

3. A compressor according to claim 1, wherein the rotatable shaft is connected to said circular eccentric and imparts rotational motion to said circular eccentric.

4. A compressor according to claim 1, wherein the rotatable shaft imparts rotational motion to said at least a first piston rod.

5. A compressor according to claim 1, wherein said at least a first piston rod is unitary.

6. A compressor according to claim 2, wherein said at least a first piston rod is unitary.

7. A compressor according to claim 1, wherein said at least a first piston rod is supported solely by said first pair of pistons.

8. A compressor according to claim 2, wherein said at least a first piston rod is supported solely by said first pair of pistons.

9. A compressor according to claim 6, wherein said at least a first piston rod is supported solely by said first pair of pistons.

10. A compressor comprising:
    a rotatable shaft;
    a first piston rod extending through the compressor in one direction substantially perpendicular to said rotatable shaft and connecting a first pair of pistons at opposite ends of said first piston rod, said first piston rod moving back and forth relative to said rotatable shaft;
    a second piston rod extending through the compressor in another direction substantially perpendicular to said rotatable shaft and connecting a second pair of pistons at opposite ends of said second piston rod, said second piston rod moving back and forth relative to said rotatable shaft;
    a circular eccentric;
    a circular ring connected to said circular eccentric via a bearing;
    a first drive pin engaging said circular ring at a first fixed position and engaging said first piston rod; and
    a second drive pin engaging said circular ring at a second fixed position and engaging said second piston rod;
    such that, when rotational motion of the shaft rotates either said piston rods and pistons or said circular eccentric, said drive pins and said piston rods move back and forth relative to said rotatable shaft.

11. A compressor according to claim 10, wherein said second piston rod is positioned adjacent said first piston rod.

12. A compressor according to claim 10, wherein said piston rods define respective openings through which said rotatable shaft extends.

13. A compressor according to claim 10, wherein the rotatable shaft is connected to said circular eccentric and imparts rotational motion to said circular eccentric.

14. A compressor according to claim 10, wherein the rotatable shaft imparts rotational motion to said piston rods.

15. A compressor according to claim 10, wherein said piston rods are each unitary.

16. A compressor according to claim 12, wherein said piston rods are each unitary.

17. A compressor according to claim 10, wherein each of said piston rods is supported solely by its connected pair of pistons.

18. A compressor according to claim 15, wherein each of said piston rods is supported solely by its connected pair of pistons.

19. A compressor according to claim 16, wherein each of said piston rods is supported solely by its connected pair of pistons.

\* \* \* \* \*